United States Patent
Ohsawa et al.

(10) Patent No.: US 7,012,067 B2
(45) Date of Patent: Mar. 14, 2006

(54) BLOOD LIPID AMELIORANT COMPOSITION

(75) Inventors: Tsuneki Ohsawa, Tokyo (JP); Ikuo Takagi, Matsudo (JP); Ippei Shimizu, Tokyo (JP); Tatsuhito Kondo, Tokyo (JP); Masato Nakayama, Saitama (JP); Yasuhiro Torizumi, Ryugasaki (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/461,775

(22) Filed: Jun. 12, 2003

(65) Prior Publication Data

US 2004/0014712 A1 Jan. 22, 2004

Related U.S. Application Data

(63) Continuation-in-part of application No. PCT/JP01/10914, filed on Dec. 12, 2001.

(30) Foreign Application Priority Data

Dec. 14, 2000 (JP) ........................................ 2000-379879

(51) Int. Cl.
  *A61K 31/7076* (2006.01)
  *A61K 31/525* (2006.01)
  *A61K 31/375* (2006.01)
  *A61K 31/366* (2006.01)

(52) U.S. Cl. ................ 514/47; 514/250; 514/460; 514/458; 514/553; 514/561; 514/474; 514/724; 536/22.1; 536/23.1; 435/4; 435/6; 424/401; 424/472; 424/59; 424/65

(58) Field of Classification Search ............... 514/47, 514/250, 460, 458, 553, 561, 474, 726; 536/22.1, 536/23.5; 435/4, 6; 424/401, 472, 59, 65
See application file for complete search history.

(56) References Cited

U.S. PATENT DOCUMENTS 6,245,797 B1 * 6/2001 Winokur ..................... 514/406

6,693,129 B1 * 2/2004 Rath ............................ 514/474

FOREIGN PATENT DOCUMENTS

| EP | 933080 A | 8/1999 |
|---|---|---|
| JP | 55-76816 A | 6/1980 |
| JP | 58-69813 A | 4/1983 |
| JP | 60-41611 A | 3/1985 |
| WO | WO 94/15592 A1 | 7/1994 |
| WO | WO 97/38694 A1 | 10/1997 |
| WO | WO 97/38694 | * 10/1997 |

OTHER PUBLICATIONS

Neuteufl Thomas, "Additional benefit of vitamin E supplementation to simvastatin therapy on vasoreactivity of the brachial artery of hypercholesterolemic men," J. Am. Coll. Cardiol., vo. 32, No. 3 (1998) pp. 711–716.

Sulfur Amino Acids, vol. 7, No. 1, pp. 201–205 (1984).

Geriat. Med., vol. 19, No. 3, 415–422 (1981).

Suzumura et al., "Inhibitory Effects of Fluvastatin and Its Metabolites on Hydrogen Peroxide–Induced Oxidative Destruction on Hemin and Low–Density Lipoprotein", *Biol. Pharm. Bull.* 23 (7) 973–878, Jul. 2000.

Cighetti et al., "Modulation of HMG–CoA reductase activity by pantetheine/pantethine", *Biochimica et Biophysica Acta*, 963(2), 389–393, Nov. 25, 1988.

Bellentani et al., "Taurine increases bile acid pool size and redues bile saturation index in the hamster", *Journal of Lipid Research*, vol. 28(9), 1021–1027, Sep. 1987.

* cited by examiner

*Primary Examiner*—James O. Wilson
*Assistant Examiner*—Devesh Khare
(74) *Attorney, Agent, or Firm*—Frishauf, Holtz, Goodman & Chick, P.C.

(57) ABSTRACT

A blood lipid ameliorating composition containing simvastatin and one or more ingredients selected from a riboflavin compound, a d-α-tocopherol compound, an ascorbic acid compound, pantethine, and taurine.

33 Claims, No Drawings

BLOOD LIPID AMELIORANT COMPOSITION

This is a continuation-in-part of PCT/JP01/10914 filed Dec. 12, 2001.

BACKGROUND OF THE INVENTION

The present invention relates to a blood lipid ameliorating composition that contains simvastatin in combination with one or more ingredients selected from the group consisting of a riboflavin derivative, a tocopherol derivative, an ascorbic acid derivative, pantethine, and taurine.

Since an increase in blood lipid peroxide levels causes damage to endothelial cells, enhances platelet aggregation, and promotes foam cell forming, all of which contribute to arteriosclerosis, lipid peroxide-lowering agents are useful agents.

Simvastatin reduces total cholesterol levels in the blood by inhibiting HMG-CoA reductase activity. Furthermore, it is known that simvastatin reduces lipid peroxide levels in the blood.

The anti-oxidative actions of riboflavin derivatives, tocopherol derivatives, and ascorbic acid derivatives are well known. Furthermore, it is known that pantethine and taurine reduce lipid peroxide levels in the blood (References: Sulfur Amino Acids, Vol. 7, No.1, 1984, p. 201–205; Geriatr. Med., Vol. 19, No. 3, p. 415–422).

BRIEF DESCRIPTION OF THE INVENTION

The present inventors investigated drug compositions that decrease lipid peroxide levels in the blood, and found that co-administration of simvastatin with a certain vitamin or taurine reduces lipid peroxide levels in the blood, and completed the present invention.

The present invention comprises a blood lipid ameliorating composition which contains simvastatin in combination with one or more ingredients selected from the group consisting of a riboflavin derivative, a tocopherol derivative, an ascorbic acid derivative, pantethine, and taurine. The present invention also comprises the use of this composition to ameliorate blood lipid levels.

DETAILED DESCRIPTION OF THE INVENTION

The term 'simvastatin' includes (+)-(1S,3R,7S,8S,8aR)-1,2,3,7,8,8a-hexahydro-3,7-dimethyl-8-[2-[(2R4R)-tetrahydro-4-hydroxy-6-oxo-2H-pyran-2-yl]ethyl]-1-naphthyl 2,2-dimethylbutanoate, salts thereof (particularly the sodium salt), and the free acid.

The term 'riboflavin derivative' includes riboflavin and riboflavin acid esters such as riboflavin butyrate. Among these compounds, riboflavin, riboflavin sodium phosphate, riboflavin butyrate, flavin-adenine dinucleotide, or flavin-adenine dinucleotide sodium salt are preferred compounds. Furthermore, riboflavin sodium phosphate and riboflavin butyrate are more preferred and riboflavin butyrate is the most preferred compound.

The term 'tocopherol derivative' includes acid esters of tocopherol such as tocopherol (racemate and its optical enantiomers) and tocopherol acetate (racemate and its optical enantiomers). Among these compounds d-α-tocopherol succinate, dl-α-tocopherol succinate, dl-α-tocopherol calcium succinate, d-α-tocopherol acetate, dl-α-tocopherol acetate, d-α-tocopherol, or dl-α-tocopherol are preferred compounds. Furthermore, dl-α-tocopherol succinate or d-α-tocopherol acetate are more preferred and particularly d-α-tocopherol acetate is the most preferred compound.

The term 'ascorbic acid derivative' includes ascorbic acid, ascorbates such as sodium ascorbate and ascorbic acid esters such stearyl ascorbate. Among these compounds ascorbic acid, sodium ascorbate or calcium ascorbate are preferred compounds and ascorbic acid is the more preferred compound.

Pantethine is 2,4-dihydroxy-N-[3-[(2-mercaptoethyl)amino]-3-oxopropyl]-3,3-dimethylbutanamide.

The term 'taurine' indicates 2-aminoethanesulfonic acid and salts thereof.

Blood lipid peroxides are lipid peroxides located in the blood, and involve hyperoxidated LDL (low-density lipoproteins) and so on.

The term "ameliorating" in the expression "a blood lipid ameliorating agent" indicates that the levels are decreased by clinically significant amounts following administration of the agent.

The weight percent of simvastatin contained in solid preparations of the present invention of the blood lipid ameliorating composition is 0.005 to 3%, preferably 0.03 to 2%.

The weight percent of riboflavin derivative in the solid preparations is typically 0.002 to 40%, preferably 0.01 to 20.0%. Furthermore, the weight percent of ascorbic acid derivative is typically 0.05 to 50%, preferably 0.5 to 25.0%. The weight percent of tocopherol derivative is typically 0.002 to 40.0%, preferably 0.02 to 20%, the weight percent of pantethine is typically 0.3 to 50%, preferably 1.0 to 20%, and that of taurine is typically 0.3 to 50%, preferably 1 to 25%.

The content of simvastatin contained in liquid and solution preparations of the blood lipid ameliorating composition of the present invention is typically 0.03 to 1 mg/mL, and preferably 0.05 to 0.5 mg/mL; that of riboflavin derivative is typically 0.05 to 5 mg/mL, preferably 0.1 to 3 mg/mL. In addition, the content of ascorbic acid derivative is typically 1 to 20 mg/mL, preferably 2 to 10 mg/mL. The content of tocopherol derivative is typically 0.5 to 5 mg/mL, preferably 1.5 to 3 mg/mL. The content of pantethine is typically 0.5 to 20 mg/mL, preferably 1 to 10 mg/mL; and that of taurine is typically 1.0 to 50 mg/mL, preferably 2 to 35 mg/mL.

Practical preparations of the drug composition to reduce lipid peroxide levels in the blood are tablets, granules (involving powders), capsules, and liquids and solutions, etc., and are manufactured following addition of the required additive agents or materials, if necessary, according to conventional methods described in The Pharmacopeia of Japan.

In the preparations described above, additive agents that are conventionally used can be employed based on the preparation.

For instance, in the case of tablets, lactose and crystalline cellulose are used as a diluent, magnesium aluminometasilicate, etc., are used as a stabilizing agent, hydroxypropylcellulose, etc., are used as a binder, and magnesium stearate is used as a lubricant.

In granules and capsules, lactose and purified sucrose are used as a diluent, magnesium aluminometasilicate is used as a stabilizing agent, cornstarch, etc., are used as an adsorbent, and hydroxypropylcellulose and polysorbate, etc., are used as a binder.

In liquids and solutions, D-sorbitol solution and honey, etc., are used as a sweetener, dl-malic acid, etc., are used as a flavoring agent, disodium dihydrogen ethylenediamine tetraacetate, etc., are used as a stabilizing agent, ethanol is used as a co-solvent, and polyoxyethylene hydrogenated castor oil stearate 60, etc., are used as a solubilizer.

In the preparations described above, a disintegrator such as crospovidone, etc.; an adsorbent such as calcium silicate, etc.; a coloring agent such as red ferric oxide and caramel, etc.; a pH modifier such as sodium benzoate, etc.; and a flavor may be used if necessary.

When the composition in the present invention is administered, each component of the composition can be administered at the same time or individually at certain intervals.

The term "administration at the same time" described above has no particular limitation, provided that the preparations of the components are administered at roughly the same time. However, it is desirable that a single composition containing all components is administered.

The term "administration of individual components at certain intervals" described above has no particular limitation, provided that each component is individually administered at different times. In this case, one component is administered and the other components can be administered within a certain defined time period.

In the case that 3 or more components in total are contained in the composition, the term "administration of these components at the same time or individually at different times" described above involves the following means of administration: all components are administered at the same time; all components are administered individually at different times; 2 or more components are administered at the same time and the remaining component(s) are administered at different times; and 2 or more components are administered at different times and the remaining components are administered at the same time, and so on.

EXAMPLES

The present invention is described in more detail by way of the following examples. However, the present invention is not limited to these examples.

Test Example 1
Tablets
(1) Composition

TABLE 1

|  | RFV 4 tabs (800 mg) | AA 4 tabs (1200 mg) | Tocoph 4 tabs (900 mg) | Pant 4 tabs (1200 mg) | Taurine 4 tabs (1200 mg) |
|---|---|---|---|---|---|
| Simvastatin | 10 mg | 10 mg | 10 mg | 10 mg | 10 mg |
| RFVb | 100 mg | — | — | — | — |
| Ascorbic acid | — | 500 mg | — | — | — |
| dl-α-Tocopherol succinate | — | — | 200 mg | — | — |
| Pantethine | — | — | — | 500 mg | — |
| Taurine (Aminoethanesulfonic acid) | — | — | — | — | 500 mg |
| Crystalline cellulose | 120 mg | 12 mg | 12 mg | 12 mg | 120 mg |
| Magnesium aluminometasilicate | 144 mg | — | — | — | 144 mg |
| Sucrose esters fatty acids | — | 140 mg | 108 mg | 140 mg | — |
| Hydroxypropylcellulose | 96 mg | 48 mg | 48 mg | 48 mg | 96 mg |
| Magnesium stearate | 24 mg | 24 mg | 24 mg | 24 mg | 24 mg |
| Crospovidone | 100 mg | 48 mg | 48 mg | 48 mg | 48 mg |
| Lactose | aq | aq | aq | aq | aq |

RFVb: Riboflavin butyrate, RFV: Riboflavin, AA: Ascorbic acid, Tocoph: Tocopherol, Pant: Pantethine, tabs: tablets, aq: appropriate quantity (2) Manufacturing Methods The amount of each component described above is weighed and prepared according to the methods described in the "General Rules for Preparations of Tablets" in "The Pharmacopeia of Japan".

Test Example 2

Granules
(1) Composition

TABLE 2

|  | RFV 4 packs (4 g) | AA 4 packs (5.2 g) | Tocoph 4 packs (4.2 g) | Pant 4 packs (4.6 g) | Taurine 4 packs (5.2 g) |
|---|---|---|---|---|---|
| Simvastatin | 10 mg | 10 mg | 10 mg | 10 mg | 10 mg |
| RFVb | 100 mg | — | — | — | — |
| Ascorbic acid | — | 1.0 g | — | — | — |
| dl-α-Tocopherol succinate | — | — | 200 mg | — | — |
| Pantethine | — | — | — | 500 mg | — |
| Taurine (Aminoethanesulfonic acid) | — | — | — | — | 1.0 g |
| Purified sucrose | 1.4 g | 1.6 g | 1.4 g | 1.6 g | 1.4 g |
| Stevia extracts | — | 16 mg | — | 16 mg | — |
| Cornstarch | 1.2 g | 1.2 g | 1.2 g | 1.2 g | 1.2 g |
| Polysorbate 80 | 80 mg | 48 mg | 48 mg | 48 mg | 80 mg |
| Magnesium aluminometasilicate | 144 mg | — | 128 mg | — | 144 mg |
| Magnesium stearate | 24 mg | 24 mg | 24 mg | 24 mg | 24 mg |
| Lactose | aq | aq | aq | aq | aq |

RFVb: Riboflavin butyrate, RFV: Riboflavin, AA: Ascorbic acid, Tocoph: Tocopherol, Pant: Pantethine, packs: packages, aq: appropriate quantity (2) Manufacturing Methods The amount of each component described above is weighed and prepared according to the methods described in the "General Rules for Preparations of Granules" in "The Pharmacopeia of Japan".

Test Example 3
Capsules
(1) Components

TABLE 3

|  | RFV 4 caps | AA 4 caps | Tocoph 4 caps | Pant 4 caps | Taurine 4 caps |
|---|---|---|---|---|---|
| Simvastatin | 10 mg | 10 mg | 10 mg | 10 mg | 10 mg |
| RFVb | 100 mg | — | — | — | — |
| AA | — | 500 mg | — | — | — |
| dl-α-Tocopherol succinate | — | — | 200 mg | — | — |
| Pantethine | — | — | — | 500 mg | — |
| Taurine (Aminoethanesulfonic acid) | — | — | — | — | 500 mg |
| Cornstarch | 960 mg | 960 mg | 840 mg | 960 mg | 960 mg |
| Polysorbate 80 | 80 mg | 48 mg | 48 mg | 48 mg | 80 mg |
| Magnesium aluminometasilicate | 144 mg | — | 128 mg | — | 144 mg |
| Magnesium stearate | 24 mg | 24 mg | 24 mg | 24 mg | 24 mg |
| Lactose | aq | aq | aq | aq | aq |
| Subtotal | 1520 mg | 1940 mg | 1580 mg | 1940 mg | 2008 mg |
| Capsule | 320 mg | 640 mg | 320 mg | 640 mg | 640 mg |
| Total | 1840 mg | 2580 mg | 1900 mg | 2580 mg | 2648 mg |

RFVb: Riboflavin butyrate, RFV: Riboflavin, AA: Ascorbic acid, Tocoph: Tocopherol, Pant: Pantethine, caps: capsules, aq: appropriate quantity (2) Manufacturing Methods
The amount of each component described above is weighed and prepared according to the methods described in the "General Rules for Preparations of Granules" in "The Pharmacopeia of Japan", and hard capsules are prepared by filling the granules into capsules.

Test Example 4
Liquids and Solutions
(1) Components

TABLE 4

|  | RFV 100 mL | AA 100 mL | Tocoph 100 mL | Pant 100 mL | Taurine 100 mL |
|---|---|---|---|---|---|
| Simvastatin | 10 mg | 10 mg | 10 mg | 10 mg | 10 mg |
| RFV sodium | 200 mg | — | — | — | — |
| Ascorbic acid | — | 500 mg | — | — | — |
| dl-α-Tocopherol acetate | — | — | 50 mg | — | — |
| Pantethine | — | — | — | 500 mg | — |
| Taurine (Aminoethanesulfonic acid) | — | — | — | — | 500 mg |
| D-Sorbitol solution | 4 g | 6 g | 4 g | 6 g | 4 g |
| Honey | 7 g | 8 g | 7 g | 8 g | 7 g |
| dl-Malic acid | 200 mg | — | 200 mg | — | 200 mg |
| DDEDTA | 20 mg | 20 mg | 20 mg | 20 mg | 20 mg |
| Ethanol | 2 mL | 2 mL | 2 mL | 2 mL | 2 mL |
| PEHCO | 100 mg | 100 mg | 100 mg | 100 mg | 100 mg |
| Sodium benzoate | 60 mg | 60 mg | 60 mg | 60 mg | 60 mg |
| Flavor | trace | trace | trace | trace | trace |
| Distilled water | aq | aq | aq | aq | aq |

RFV: Riboflavin, AA: Ascorbic acid, Tocoph: Tocopherol, Pant: Pantethine, D-Sorbitol solution: D-Sorbitol solution (70%), DDEDTA: Disodium dihydrogen ethylenediamine tetraacetate, PEHCO: Polyoxyethylene hydrogenated castor oil stearate 60, aq: appropriate quantity (2) Manufacturing Methods
The amount of each component described above is weighed and prepared according to the methods described in the "General Rules for Preparations of Liquids and Solutions" in "The Pharmacopeia of Japan".

Assay of Blood Lipid Ameliorating Effects
Test Methods
(1) Test Compounds
Simvastatin was synthesized at Chemtech Labo., Inc. and riboflavin butyrate, d-α-tocopherol acetate, ascorbic acid, pantethine, and taurine were purchased from Mitsubishi-Tokyo Pharmaceutical Inc., Eisai Co., Ltd., NIPPON ROCHE K.K., Nacalai Tesque, Inc., and Dai-ich Pharmaceutical Co., Ltd., respectively.

(2) Test Animals
Beagle dogs aged 5 months were purchased from Covance Research Products Inc. and used after 1 month of quarantine and acclimatisaton breeding.

(3) Preparation Forms for Administration, Methods for Preparation of the Formulation, and Method for Stocking the Formulation
The required amounts of simvastatin or each component of the combination drug calculated from the body weight of each dog were weighed and filled in a gelatin capsule (½ ounce) purchased from TORPAC Inc. Capsules filled with simvastatin were stocked in a refrigerator and those filled with combination drugs stocked at room temperature until use.
The combination drugs were filled in identical gelatin capsules.

(4) Route of Administration and Administration Period
Simvastatin or combination drug capsules were forcibly orally administered to each of the test animals once daily between 9:00 and 12:30. Animals were fasted for 2 or 3 hr prior to administration of the capsules.
The administration period was 11 successive days.

(5) Preparation of Test Samples and Procedures
Blood (10 mL) was collected from the superficial radial vein 2 or 1 weeks prior to administration and 4, 8, and 12 days after administration was started. Animals were fasted for approximately 18 hr prior to blood collection. Collected blood was placed in a test tube and left at room temperature for 0.5–1 hr, before being centrifuged (3,000 rpm for 10 min). The obtained serum was used for assays of blood levels of lipid peroxides, total cholesterol, triglycerides, free fatty acids, GOT, and CPK according to Yagi's methods, CEH-COD-POD methods, GK-GPO-POD methods, ACS-ACOD methods, UV-rate methods, and UV-rate methods, respectively. (For ACS-ACOD (Acyl-CoA synthetase-Acyl-CoA oxidase peroxidase) methods, CEH-COD-POD (Cholesterol ester hydrolase-Cholesteroloxidase-Peroxidase) methods, Yagis methods and GK-GPO-POD (Glycerokinase-Glycerolphosphateoxidase-Peroxidase) methods, see: Kanai's Manual of Clinical Laboratory Medicine; 31$^{st}$ Edition (September 1998), Kanehara & Co., Ltd.)

All these levels were determined using a fluorometer (Hitachi, Ltd., F3000), a full automatic analyzer (Monarch, Instrumentation Laboratory), and an automatic analyzer (7170, Hitachi, Ltd.).

RESULTS

Lipid peroxide levels, etc. in the blood collected from dogs treated with either simvastatin, ascorbic acid, riboflavin butyrate, d-α-tocopherol acetate, pantethine or taurine were determined. The levels of lipid peroxides and other substances described above in the blood collected from dogs co-administered with simvastatin and a composition which contains one or more substances selected from riboflavin butyrate, d-α-tocopherol acetate, ascorbic acid, pantethine and taurine were also similarly determined. All these values in dogs treated with one of the drugs described above were converted to their relative ratios against their averaged pre-dosing levels (100) determined 2 and 1 weeks prior to drug administration. The averaged value in each group was obtained from 5 animals per group.

(Effects of Co-administration of Simvastatin and Riboflavin Butyrate)

TABLE 5

| | | Blood Lipid Peroxide Levels after administration | | |
|---|---|---|---|---|
| Test Substance | Dose (mg/kg) | 4 days | 8 days | 12 days |
| Simvastatin alone | 1 | 96.2 | 86.4 | 91.0 |
| RFVb alone | 200 | 88.9 | 101.0 | 80.8 |
| Simvastatin + RFVb | 1 200 | 89.5 | 75.9 | 84.8 |

RFVb: riboflavin butyrate

TABLE 6

| | | Blood FFA Levels after administration | | |
|---|---|---|---|---|
| Test Substance | Dose (mg/kg) | 4 days | 8 days | 12 days |
| Simvastatin alone | 1 | 93.8 | 99.3 | 97.0 |
| RFVb alone | 200 | 97.6 | 101.2 | 92.9 |
| Simvastatin + RFVb | 1 200 | 102.6 | 84.3 | 72.4 |

RFVb: riboflavin butyrate, FFA: Free Fatty Acids (Effects of Co-administration of Simvastatin and d-α-tocopherol Acetate)

TABLE 7

| | | Blood Triglyceride Levels after administration | | |
|---|---|---|---|---|
| Test Substance | Dose (mg/kg) | 4 days | 8 days | 12 days |
| Simvastatin alone | 1 | 96.2 | 86.4 | 91.0 |
| Tocoph alone | 300 | 106.3 | 119.0 | 75.9 |
| Simvastatin + Tocoph | 1 300 | 85.1 | 67.2 | 75.2 |

Tocoph: d-α-tocopherol acetate

TABLE 8

| | | Blood FFA Levels after administration | | |
|---|---|---|---|---|
| Test Substance | Dose (mg/kg) | 4 days | 8 days | 12 days |
| Simvastatin alone | 1 | 93.8 | 99.3 | 97.0 |
| Tocoph alone | 300 | 115.4 | 103.1 | 86.2 |
| Simvastatin + Tocoph | 1 300 | 94.3 | 95.7 | 81.6 |

FFA: Free Fatty Acid, Tocoph: d-α-tocopherol acetate

TABLE 9

| | | GOT Levels after administration | | |
|---|---|---|---|---|
| Test Substance | Dose (mg/kg) | 4 days | 8 days | 12 days |
| Simvastatin alone | 1 | 98.1 | 93.9 | 100.4 |
| Tocoph alone | 300 | 114.9 | 139.7 | 109.1 |
| Simvastatin + Tocoph | 1 300 | 89.1 | 85.6 | 89.1 |

FFA: Free Fatty Acid, Tocoph: d-α-tocopherol acetate (Effects of Co-administration of Simvastatin and Ascorbic Acid)

TABLE 10

| | | Blood Lipid Peroxide Levels after administration | | |
|---|---|---|---|---|
| Test Substance | Dose (mg/kg) | 4 days | 8 days | 12 days |
| Simvastatin alone | 1 | 96.2 | 86.4 | 91.0 |
| Ascorbic acid alone | 500 | 87.6 | 89.9 | 94.4 |
| Simvastatin + Ascorbic acid | 1 500 | 85.3 | 75.7 | 78.9 |

TABLE 11

| | | Blood FFA Levels after administration | | |
|---|---|---|---|---|
| Test Substance | Dose (mg/kg) | 4 days | 8 days | 12 days |
| Simvastatin alone | 1 | 93.8 | 99.3 | 97.0 |
| Ascorbic acid alone | 500 | 87.4 | 109.6 | 97.8 |
| Simvastatin + Ascorbic acid | 1 500 | 82.8 | 76.1 | 69.5 |

FFA: Free Fatty Acid

TABLE 12

| | | CPK Levels after administration | | |
|---|---|---|---|---|
| Test Substance | Dose (mg/kg) | 4 days | 8 days | 12 days |
| Simvastatin alone | 1 | 94.5 | 99.4 | 91.0 |
| Ascorbic acid alone | 500 | 98.3 | 95.1 | 91.5 |
| Simvastatin + Ascorbic acid | 1 500 | 90.6 | 88.8 | 89.3 |

(Effects of Co-administration of Simvastatin and Pantethine)

TABLE 13

| Test Substance | Dose (mg/kg) | Blood Lipid Peroxide Levels after administration | | |
|---|---|---|---|---|
| | | 4 days | 8 days | 12 days |
| Simvastatin alone | 1 | 96.2 | 86.4 | 91.0 |
| Pantethine alone | 300 | 82.5 | 105.0 | 87.5 |
| Simvastatin + Pantethine | 1 300 | 83.8 | 75.4 | 75.9 |

TABLE 14

| Test Substance | Dose (mg/kg) | Blood Triglyceride Levels after administration | | |
|---|---|---|---|---|
| | | 4 days | 8 days | 12 days |
| Simvastatin alone | 1 | 97.6 | 88.9 | 89.3 |
| Pantethine alone | 300 | 104.4 | 103.9 | 96.6 |
| Simvastatin + Pantethine | 1 300 | 98.9 | 84.8 | 83.9 |

(Effects of Co-administration of Simvastatin and Taurine)

TABLE 15

| Test Substance | Dose (mg/kg) | Blood Lipid Peroxide Levels after administration | | |
|---|---|---|---|---|
| | | 4 days | 8 days | 12 days |
| Simvastatin alone | 1 | 96.2 | 86.4 | 91.0 |
| Taurine alone | 1000 | 95.8 | 93.8 | 87.5 |
| Simvastatin + Taurine | 1 1000 | 83.8 | 76.2 | 80.5 |

TABLE 16

| Test Substance | Dose (mg/kg) | Blood Total Cholesterol Levels after administration | | |
|---|---|---|---|---|
| | | 4 days | 8 days | 12 days |
| Simvastatin alone | 1 | 102.1 | 93.2 | 86.6 |
| Taurine alone | 1000 | 95.9 | 90.2 | 87.2 |
| Simvastatin + Taurine | 1 1000 | 98.6 | 79.0 | 74.8 |

TABLE 17

| Test Substance | Dose (mg/kg) | Blood Triglyceride Levels after administration | | |
|---|---|---|---|---|
| | | 4 days | 8 days | 12 days |
| Simvastatin alone | | 97.6 | 88.9 | 89.3 |
| Taurine alone | 1000 | 98.6 | 95.8 | 80.8 |
| Simvastatin + Taurine | 1 1000 | 97.2 | 77.1 | 71.4 |

The present invention, drug compositions of simvastatin in combination with ascorbic acid and so forth, exhibits excellent blood lipid peroxide-lowering effects and is useful as a blood lipid ameliorating agent.

Although the dose of compounds used according to the invention may widely vary depending on the extent of diseases and age of patients, (e.g. human patients), the dose of one administration of simvastatin is normally within the range of from 0.005 mg/kg to 5 mg/kg, preferably from 0.05 mg/kg to 0.5 mg/kg, administered once or several times a day dependent on the extent of diseases.

The dose of one administration of riboflavin derivative is normally within the range of from 0.004 mg/kg to 24 mg/kg, preferably from 0.04 mg/kg to 2.4 mg/kg, administered once or several times a day dependent on the extent of diseases.

The dose of one administration of tocopherol derivative is normally within the range of from 0.02 mg/kg to 60 mg/kg, preferably from 0.2 mg/kg to 6.0 mg/kg, administered once or several times a day dependent on the extent of diseases.

The dose of one administration of ascorbic acid derivative is normally within the range of from 0.1 mg/kg to 400 mg/kg, preferably from 1 mg/kg to 40 mg/kg, administered once or several times a day dependent on the extent of diseases.

The dose of one administration of pantethine is normally within the range of from 0.06 mg/kg to 120 mg/kg, preferably from 0.6 mg/kg to 12 mg/kg, administered once or several times a day dependent on the extent of diseases.

The dose of one administration of taurine is normally within the range of from 1 mg/kg to 600 mg/kg, preferably from 10 mg/kg to 60 mg/kg, administered once or several times a day dependent on the extent of diseases.

What is claimed is:

1. A method of lowering lipid peroxide levels in the blood, said method comprising administering, in combination, to a warm-blooded animal in need thereof, in amounts effective to ameliovate said blood lipid levels, simvastatin and one or more agents selected from the group consisting of a riboflavin derivative selected from the group consisting of riboflavin, riboflavin sodium phosphate, riboflavin butyrate, flavin-adenine dinucleotide and flavin-adenine dinucleotide sodium salt; a tocopherol derivative selected from the group consisting of d-α-tocopherol succinate, dl-α-tocopherol succinate, dl-α-tocopherol calcium succinate, d-α-tocopherol acetate, dl-α-tocopherol acetate, d-α-tocopherol and dl-α-tocopherol; an ascorbic acid derivative, selected from the group consisting of ascorbic acid, sodium ascorbate, calcium ascorbate and stearyl ascorbate; pantethine and taurine.

2. A method according to claim 1 wherein said simvastatin and said one or more agents selected from the group consisting of said riboflavin derivative, said tocopherol derivative, said ascorbic acid derivative, said pantethine and said taurine, are administered in the form of a combination pharmaceutical composition.

3. A method according to claim 1 wherein said simvastatin and said one or more agents selected from the group consisting of said riboflavin derivative, said tocopherol derivative, said ascorbic acid derivative, said pantethine, and said taurine are administered separately and simultaneously.

4. A method according to claim 1 wherein said simvastatin and said one or more agents selected from the group consisting of said riboflavin derivative, said tocopherol derivative, said ascorbic acid derivative, said pantethine and said taurine, are administered separately and non-simultaneously.

5. A method according to claim 1 wherein the agent is said riboflavin derivative which is selected from the group consisting of riboflavin, flavin-adenine dinucleotide and flavin-adenine dinucleotide sodium salt.

6. A method according to claim 1 wherein the agent is said riboflavin derivative which is riboflavin sodium phosphate.

7. A method according to claim 1 wherein the agent is said riboflavin derivative which is riboflavin butyrate.

8. A method according to claim 1 wherein the agent is said tocopherol derivative which is selected from the group consisting of dl-α-tocopherol succinate, dl-α-tocopherol calcium succinate, dl-α-tocopherol acetate, d-α-tocopherol and dl-α-tocopherol.

9. A method according to claim 1 wherein the agent is said tocopherol derivative which is d-α-tocopherol succinate.

10. A method according to claim 1 wherein the agent is said tocopherol derivative which is d-α-tocopherol acetate.

11. A method according to claim 1 wherein the agent is said ascorbic acid derivative which is selected from the group consisting of sodium ascorbate and calcium ascorbate.

12. A method according to claim 1 wherein the agent is said ascorbic acid derivative which is ascorbic acid.

13. A method according to claim 1, said method comprising administering, in combination, to a warm-blooded animal in need thereof, in amounts effective in ameliorating said blood lipid levels, simvastatin and riboflavin succinate.

14. A method according to claim 13 wherein said simvastatin and said riboflavin succinate are administered in the form of a combination pharmaceutical composition.

15. A method according to claim 13 wherein said simvastatin and said riboflavin succinate are administered separately and simultaneously.

16. A method according to claim 13 wherein said simvastatin and said riboflavin succinate are administered separately and non-simultaneously.

17. A method according to claim 1, said method comprising administering, in combination, to a warm-blooded animal in need thereof, in amounts effective to ameliovate said blood lipid levels, simvastatin and ascorbic acid.

18. A method according to claim 17 wherein said simvastatin and said ascorbic acid are administered in the form of a combination pharmaceutical composition.

19. A method according to claim 17 wherein said simvastatin and said ascorbic acid are administered separately and simultaneously.

20. A method according to claim 17 wherein said simvastatin and said ascorbic acid are administered separately and non-simultaneously.

21. A method according to claim 1, said method comprising administering, in combination, to a warm-blooded animal in need thereof, in amounts effective to ameliovate said blood lipid levels, simvastatin and d-α-tocopherol acetate.

22. A method according to claim 21 wherein said simvastatin and said d-α-tocopherol acetate are administered in the form of a combination pharmaceutical composition.

23. A method according to claim 21 wherein said simvastatin and said d-α-tocopherol acetate are administered separately and non-simultaneously.

24. A method according to claim 21 wherein said simvastatin and said d-α-tocopherol acetate are administered separately and non-simultaneously.

25. A method according to claim 1, said method comprising administering, in combination, to a warm-blooded animal in need thereof, in amounts effective to ameliovate said blood lipid levels, simvastatin and pantethine.

26. A method according to claim 25 wherein said simvastatin and said pantethine are administered in the form of a combination pharmaceutical composition.

27. A method according to claim 25 wherein said simvastatin and said pantethine are administered separately and simultaneously.

28. A method according to claim 25 wherein said simvastatin and said pantethine are administered separately and non-simultaneously.

29. A method according to claim 1, said method comprising administering, in combination, to a warm-blooded animal in need thereof, in amounts effective to ameliovate said blood lipid levels, simvastatin and taurine.

30. A method according to claim 29 wherein said simvastatin and said taurine are administered in the form of a combination pharmaceutical composition.

31. A method according to claim 29 wherein said simvastatin and said taurine are administered separately and simultaneously.

32. A method according to claim 29 wherein said simvastatin and said taurine are administered separately and non-simultaneously.

33. A method according to claim 1 wherein the warm-blooded animal is a human.

* * * * *

UNITED STATES PATENT AND TRADEMARK OFFICE
CERTIFICATE OF CORRECTION

PATENT NO. : 7,012,067 B2  Page 1 of 1
APPLICATION NO. : 10/461775
DATED : March 14, 2006
INVENTOR(S) : Ohsawa et al.

It is certified that error appears in the above-identified patent and that said Letters Patent is hereby corrected as shown below:

Title Page, right column, under "OTHER PUBLICATIONS", referring to Suzumura et al., after "*Pharm. Bull.* 23 (7)", delete "973" and insert -- 873 --.

Signed and Sealed this

Sixth Day of March, 2007

JON W. DUDAS
*Director of the United States Patent and Trademark Office*